(12) United States Patent
Hagen et al.

(10) Patent No.: US 9,810,622 B2
(45) Date of Patent: Nov. 7, 2017

(54) SAMPLE TESTING SYSTEMS AND METHODS WITH AUTOMATED CLEANING

(71) Applicant: GEN-PROBE INCORPORATED, San Diego, CA (US)

(72) Inventors: Norbert D. Hagen, Carlsbad, CA (US); Byron J. Knight, San Diego, CA (US); David Opalsky, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 0 days.

(21) Appl. No.: 15/094,227

(22) Filed: Apr. 8, 2016

(65) Prior Publication Data

US 2016/0299056 A1 Oct. 13, 2016

Related U.S. Application Data

(60) Provisional application No. 62/145,247, filed on Apr. 9, 2015.

(51) Int. Cl.
| | |
|---|---|
| *G01N 21/15* | (2006.01) |
| *G01N 35/00* | (2006.01) |
| *B08B 1/00* | (2006.01) |
| *B08B 9/00* | (2006.01) |
| *G02B 6/38* | (2006.01) |

(52) U.S. Cl.
CPC .............. *G01N 21/15* (2013.01); *B08B 1/00* (2013.01); *B08B 9/00* (2013.01); *G01N 35/0092* (2013.01); *G01N 35/00623* (2013.01); *G01N 35/00871* (2013.01); *G02B 6/3866* (2013.01); *B08B 2240/02* (2013.01); *G01N 35/0099* (2013.01); *G01N 2021/152* (2013.01); *G01N 2035/00277* (2013.01)

(58) Field of Classification Search
CPC .............................. G01N 21/15; G01N 35/00
USPC ................... 422/63–67; 436/43–54
See application file for complete search history.

(56) References Cited

U.S. PATENT DOCUMENTS

| | | | | |
|---|---|---|---|---|
| 3,962,041 A | * | 6/1976 | Muller | C12M 41/36 356/441 |
| 4,240,751 A | * | 12/1980 | Linnecke | B01L 3/5085 250/227.11 |

(Continued)

FOREIGN PATENT DOCUMENTS

| | | |
|---|---|---|
| CN | 202803688 U | 3/2013 |
| JP | 11-248630 A | 9/1999 |

OTHER PUBLICATIONS

PCT Written Opinion, International Application No. PCT/US2016/026669, Jul. 6, 2016.

(Continued)

*Primary Examiner* — Arlen Soderquist
(74) *Attorney, Agent, or Firm* — Charles B. Cappellari; David T. Burse

(57) ABSTRACT

A sample testing system includes a test receptacle support structure, an optical element positioned for transmitting electromagnetic radiation emitted or reflected by a sample disposed in a test receptacle supported by the test receptacle support structure, a cleaning member, and an automated transport arm configured to (i) detachably couple the cleaning member, (ii) move the detachably-coupled cleaning member into a position proximate to and/or contacting the optical element, and (iii) decouple the cleaning member.

24 Claims, 14 Drawing Sheets

(56) References Cited

U.S. PATENT DOCUMENTS

| | | | |
|---|---|---|---|
| 5,439,649 A | 8/1995 | Tseung et al. | |
| 5,919,706 A * | 7/1999 | Tajima | G01F 23/292 422/106 |
| 6,083,763 A * | 7/2000 | Balch | B01J 19/0046 422/105 |
| 6,125,227 A | 9/2000 | Cox | |
| 6,165,281 A | 12/2000 | Yoon | |
| 7,198,755 B2 * | 4/2007 | Tokhtuev | G01N 21/645 422/50 |
| 7,685,668 B2 | 3/2010 | Tourigny | |
| 8,151,396 B2 * | 4/2012 | Ikeda | B08B 1/00 15/102 |
| 8,828,728 B2 * | 9/2014 | Clark | G01N 21/77 119/268 |
| 2003/0048445 A1 * | 3/2003 | Tokhtuev | G01N 21/645 356/411 |
| 2007/0243008 A1 | 10/2007 | Vogt | |
| 2008/0014610 A1 * | 1/2008 | Kamata | B01L 3/502 435/69.1 |
| 2008/0193095 A1 * | 8/2008 | Chen | G02B 6/389 385/135 |
| 2009/0025160 A1 * | 1/2009 | Ikeda | B08B 1/00 15/102 |
| 2013/0168327 A1 * | 7/2013 | Clark | G01N 21/77 210/739 |
| 2013/0229650 A1 | 9/2013 | Wilson et al. | |
| 2014/0038192 A1 * | 2/2014 | Buse | C12Q 1/686 435/6.12 |
| 2016/0032358 A1 * | 2/2016 | Buse | G01N 35/04 435/6.12 |

OTHER PUBLICATIONS

PCT Search Report, International Application No. PCT/US2016/026669, Jul. 6, 2016.

* cited by examiner

SAMPLE TESTING SYSTEMS AND METHODS WITH AUTOMATED CLEANING

CROSS-REFERENCE TO RELATED APPLICATIONS

This application claims the benefit of U.S. Provisional Application No. 62/145,247, filed Apr. 9, 2015, the contents of which are hereby incorporated by reference herein.

FIELD

Embodiments of the present disclosure relate generally to systems, apparatuses, devices, and methods for performing automated biochemical assays, including nucleic acid-based assays, using optical elements, such as optical fibers, to transmit electromagnetic radiation reflected and/or emitted by samples contained in test receptacles, including automated cleaning of such optical elements and/or other system components.

BACKGROUND

Exemplary systems, apparatuses and methods for performing automated biochemical assays employing optical fibers to transmit electromagnetic radiation reflected and/or emitted by samples contained in test receptacles, are disclosed and described, by way of non-limiting examples, in each of U.S. Published Patent Application No. US 2014-0263984 A1, entitled "Indexing Signal Detection Module"; International Application No. WO 2014/153193 A2, entitled "Diagnostic Systems and Methods"; U.S. Published Patent Application No. No. US 2014-0263153 A1, entitled "Interlocking Cap and Receptacle for Automated Processes"; U.S. Published Patent Application No. US 2014-0038192 A1, entitled "System, Method and Apparatus for Automated Incubation"; and U.S. application Ser. No. 14/213,900, entitled "Method for Analyzing a Plurality of Samples," and filed on Mar. 14, 2014. The full contents of each of the foregoing applications are hereby incorporated by reference herein in their entirety.

As disclosed and described in U.S. Published Patent Application No. US 2014/0263984 A1, a "thermocycler" of an exemplary system used for performing automated fiber optic interrogation (testing) of a sample, such as a biological sample, includes a plurality of test receptacle holders (e.g., 12), each holder having a plurality of (e.g., 5) test receptacle wells. Each test receptacle well has an open bottom end, and is configured to have a test receptacle seated therein in a stable manner. By this arrangement, optical interrogation of a sample contained in a test receptacle seated in the test receptacle well may be performed using light transmitted and/or received through an axial-facing distal end of an optical fiber positioned proximate the open bottom of the respective test receptacle well.

For the test results to be reliable, it is critical that the optical pathway extending between, and including, the end surfaces of the respective optical fiber and test receptacle be free and clear of any debris, such as dust, fibers, hair and/or other particulate materials, that may interfere with the optical interrogation process. Debris can be especially problematic when the test receptacle holders are open to the atmosphere (i.e., without any cover or lid) in order to allow for easy insertion and extraction of the test receptacles into and out of the test receptacle wells. Debris may exhibit autofluorescence, i.e., in which the debris material naturally fluoresces, or may be non-fluorescent. While debris that fluoresces is generally easy to detect, debris that does not fluoresce can be difficult to detect. As a result, non-fluorescing debris can interfere with the passage of light without being detected and, consequently, lead to false or misleading test results.

As such, upon detection of any debris on or over the end of an optical fiber that may be interfering with a light signal path, the respective test receptacle well(s) and optical fiber end are not able to be used to perform further testing of sample test receptacles until they are manually cleaned, e.g., using a cotton swab or compressed air (similar to cleaning a keyboard). Furthermore, because some types of interfering debris are not readily detectable, the axial-facing ends of the optical fibers must be periodically cleaned, generally during routine servicing by a field service technician, to ensure that non-detected debris does not have an adverse effect on the sample testing. The frequency of regular cleaning can be expensive both in terms of the cleaning expense, and in terms of the lost time for testing while the system is shut-down for cleaning. Moreover, in the event immediate manual cleaning of detected debris is not performed, the respective optical fiber and/or test receptacle well are no longer available for reliable testing in the meantime, and their use must be disabled, thereby reducing the throughput of the system.

Other components of the sample testing systems may also require periodic manual cleaning and/or sterilization. For example, test receptacle wells may be exposed to sample material or reagents on the outer surfaces of receptacles, flakes of plastic, hair and/or environmental particles or contaminates, and may also require periodic manual cleaning and/or sterilization to avoid cross-contamination between samples or other problems that may arise as a result of such exposure.

None of the references described, referred to, and/or incorporated by reference herein are admitted to be prior art.

SUMMARY

In accordance with the disclosed embodiments herein, an exemplary sample testing system includes a test receptacle support structure; an optical element positioned for transmitting electromagnetic radiation emitted or reflected by a sample disposed in a test receptacle supported by the test receptacle support structure; a cleaning member; and an automated transport arm configured to detachably couple with the cleaning member, where the automated arm is further configured to move a detachably-coupled cleaning member into a position proximate to and/or contacting the optical element, and (thereafter) decouple the cleaning member. The system preferably includes a controller that controls operation of the automated transport arm for causing the automated transport arm to detachably couple with the cleaning member, and to move the detachably-coupled cleaning member into a position proximate to and/or contacting the optical element based upon one or both of a (i) predetermined cleaning schedule, and (ii) sensed presence of particulates and/or other materials disposed on or over the optical element. The automated transport arm may be an articulating arm, although this is not necessary for practicing the disclosed embodiments. In some embodiments, the automated transport arm is configured to deposit the decoupled cleaning member into a waste output. In some embodiments, the sample testing system is provided with one or more cleaning member holders, each configured to hold one or more cleaning members, where the automated transport arm may be configured to selectively deposit the decoupled cleaning member into the same or a different cleaning member holder from which the decoupled cleaning member was removed.

The cleaning member of the exemplary embodiment includes a proximal coupling element joined to a distal cleaning element, where the coupling element has a proximal end portion configured to releasably mate with a distal working end portion of the automated transport arm. The coupling element and the cleaning element may be separately molded components, in which a distal portion of the coupling element forms, by way of non-limiting examples, an interference fit or a frictional fit with a proximal portion of the cleaning element in order to subsequently join the elements together. Alternatively, the coupling element and the cleaning element may be co-molded as a single component. The automated transport arm is preferably configured to move the detachably-coupled cleaning member into a position such that the cleaning element is inserted into a test receptacle well of the test receptacle support structure, and where the cleaning element is dimensioned such that an outer surface of the cleaning element conforms to an interior surface of the test receptacle well. By way of non-limiting example, the outer surface of the cleaning element and the interior surface of the test receptacle well may have complementary, frustoconical shapes. The cleaning element preferably cleans, decontaminates and/or sterilizes the interior surface of the test receptacle well when inserted therein. In one embodiment, the test receptacle well has an open bottom, and the optical element is an optical fiber having an end positioned proximate to the open bottom of the test receptacle well, where the cleaning element cleans, decontaminates and/or sterilizes the end of the optical fiber when inserted into the test receptacle well.

In exemplary embodiments, the cleaning element may be made out of an adhesive material, such as (without limitation) silicone, platinum cured silicone, thermoplastic polyurethane, thermoplastic elastomer, thermoplastic rubber, or a gel. Additionally or alternatively, the cleaning element may be made out of a material that generates a static attraction to particulates and/or other materials that can interfere with the transmission by the optical element of electromagnetic radiation emitted or reflected by the sample, such as (without limitation) silicon, polyvinyl chloride, polypropylene, polyethylene, polyurethane, polyester or polystyrene. In other embodiments, the cleaning element may be made out of an absorbent material capable of retaining and applying a fluid substance, such as (without limitation) isopropyl alcohol, ethyl alcohol, diluted hydrochloric acid, oxalic acid, diluted sodium hydroxide and diluted sodium hypochlorite.

In one exemplary embodiment, the sample testing system includes one or more test receptacle holders, each test receptacle holder comprising a plurality of test receptacle wells, each test receptacle well having an open bottom end and configured to have a test receptacle seated therein. A plurality of optical fibers are arranged with respect to the one or more test receptacle holders, such that an end of a respective optical fiber is (or may be) positioned proximate to the open bottom end of each test receptacle well to allow for transmission of electromagnetic radiation emitted or reflected by a sample contained in a test receptacle seated in the test receptacle well. The system of this embodiment further includes a cleaning member holder comprising a plurality of cleaning member wells, each of a plurality of the cleaning member wells configured for having a cleaning member seated therein. The system further includes an automated transport arm configured to (i) detachably couple a cleaning member located in one of the cleaning member wells, (ii) remove the detachably-coupled cleaning member from the respective cleaning member well, (iii) insert a distal portion of the detachably-coupled cleaning member into one of the test receptacle wells, such that a distal end of the cleaning member is positioned proximate to or contacting the end of the optical fiber positioned proximate to the open bottom end of the respective test receptacle well, (iv) remove the detachably-coupled cleaning member from the respective test receptacle, and (v) decouple the cleaning member.

The automated transport arm is preferably configured to selectively deposit the decoupled cleaning member into the same or a different cleaning member well from which the decoupled cleaning member was removed. Alternatively and/or additionally, the automated transport arm is configured to selectively deposit the decoupled cleaning member into a waste output. The system preferably includes a controller that controls operation of the automated transport arm for causing the automated transport arm to detachably couple with a cleaning member located in a respective cleaning member well, and to move the detachably-coupled cleaning member into a position proximate to and/or contacting the one or more optical fiber ends based upon one or both of a (i) predetermined cleaning schedule, and (ii) sensed presence of particulates and/or other materials disposed on or over the optical fiber ends. Depending on the relative position of the optical fiber, the distal portion of the cleaning member of this embodiment may be dimensioned to extend to and/or through the open bottom end of the respective test receptacle well in order for the distal tip of the cleaning member to be located proximate to or in contact with the end of the respective optical fiber. The cleaning element is preferably dimensioned such that an outer surface of the cleaning element conforms to an interior surface of the test receptacle well, such that the cleaning element cleans, decontaminates and/or sterilizes one or both of (i) the interior surface of the test receptacle well, and (ii) the end of the respective optical fiber, when the cleaning element is inserted into the test receptacle well.

In accordance with another aspect of the disclosed embodiments, a cleaning member is provided for use in an automated sample testing system, the cleaning member including a proximal coupling element, and a distal cleaning element, the coupling element having a proximal end portion configured to releasably mate (e.g., by forming a frictional fit) with the working end of an automated transport arm. The coupling element and the cleaning element may be separately molded components, in which a distal portion of the coupling element forms, by way of non-limiting examples, an interference fit or a frictional fit with a proximal portion of the cleaning element in order to subsequently join the elements together. Alternatively, the coupling element and the cleaning element may be co-molded as a single component. The cleaning element is preferably dimensioned such that an outer surface of the cleaning element conforms to an interior surface of a test receptacle well of the sample testing system. By way of non-limiting example, the outer surface of the cleaning element and the interior surface of the test receptacle well may have complementary frustoconical shapes. The cleaning element may be made out of an adhesive material, such as (without limitation) silicone, platinum cured silicone, thermoplastic polyurethane, thermoplastic elastomer, thermoplastic rubber, or a gel. Additionally or alternatively, the cleaning element may be made out of a material that generates a static attraction to particulates and/or other materials that can interfere with the transmission by the optical element of electromagnetic radiation emitted or reflected by the sample, such as (without limitation) silicon, polyvinyl chloride, polypropylene, polyethylene, polyurethane, polyester or polystyrene. In other embodiments, the cleaning element may be made out of an absorbent material capable of retaining and applying a fluid substance, such as (without limitation) isopropyl alcohol, ethyl alcohol, diluted hydrochloric acid, oxalic acid, diluted sodium hydroxide and diluted sodium hypochlorite.

In accordance with further disclosed embodiments, methods for operating a sample testing system include using an automated transport arm to (i) detachably couple a cleaning member to a working end of the transport arm; (ii) move the detachably-coupled cleaning member into a position proximate to and/or contacting an optical element, such that the cleaning member thereby cleans and/or sterilizes the optical element; and (iii) decouple the cleaning member from the working end of the transport arm. In an exemplary embodiment, the test system includes a cleaning member holder having a plurality of cleaning member receptacles, the cleaning member being one of a plurality of cleaning members held in respective cleaning member receptacles of the cleaning member holder, where the automated transport arm detachably couples the cleaning member while the cleaning member is held by the respective cleaning member receptacle.

In an exemplary method, the cleaning member has a proximal coupling element and a distal cleaning element, where the automated arm detachably couples the cleaning member to the working end portion of the transport arm by detachably coupling a proximal end portion of the coupling element to the working end of the transport arm, and inserting a distal end connector of the coupling element into a recessed proximal portion of the cleaning element to thereby attach (e.g., by an interference or frictional fit) the cleaning element to the coupling element. In some such embodiments, the system includes a cleaning element holder having a plurality of cleaning element receptacles, the cleaning element being one of a plurality of cleaning elements held in respective cleaning element receptacles of the cleaning element holder. In particular, the automated transport arm inserts the distal end connector of the coupling element into the recessed proximal portion of the cleaning element while the cleaning element is held in the respective cleaning element receptacle. In such embodiments, the cleaning elements may be substantially environmentally sealed in their respective cleaning element receptacles by a frangible sealing member that is pierced when the distal end connector of the coupling element is inserted into the recessed proximal portion of the respective cleaning element.

Such method(s) may further include using the automated transport arm to move the detachably-coupled cleaning member into a position such that the cleaning element is inserted into a test receptacle well of the test receptacle support structure, wherein the cleaning element is dimensioned such that an outer surface of the cleaning element conforms to an interior surface of the test receptacle well, where the cleaning element cleans, decontaminates and/or sterilizes the interior surface of the test receptacle well when inserted therein. In an exemplary embodiment, the test receptacle well has an open bottom, and the optical element comprising an optical fiber having an end positioned proximate to the open bottom of the test receptacle well, where the cleaning element cleans, decontaminates and/or sterilizes the end of the optical fiber when inserted into the test receptacle well.

In one embodiment, the detachably-coupled cleaning member comprises a first cleaning member, and the cleaning element of the first cleaning member comprises a first cleaning element, the method further comprising, after decoupling the first cleaning member from the working end of the automated transport arm, using the automated transport arm to detachably couple a second cleaning member to the working end of the automated transport arm, the second cleaning member comprising a second cleaning element; and move the detachably-coupled second cleaning member into a position such that the second cleaning element is inserted into the same test receptacle well of the test receptacle support structure. In such embodiment, the first cleaning element may be made of a different material (e.g., an adhesive material) than the second cleaning element (e.g., made of an absorbing material and carrying a cleaning and/or sterilizing fluid).

In accordance with the disclosed methods, a controller may control operation of the automated transport arm for causing the automated transport arm to detachably couple with a respective cleaning member, and to move the respective detachably-coupled cleaning member into a position proximate to and/or contacting the optical element based upon one or both of a (i) predetermined cleaning schedule, and (ii) sensed presence of particulates and/or other materials disposed on or over the optical element. The controller may further cause the automated transport arm to deposit respective decoupled cleaning members into a system waste output or a designated used cleaning member holder.

Other and further aspects and features of embodiments will become apparent from the ensuing detailed description in view of the accompanying figures.

BRIEF DESCRIPTION OF THE DRAWINGS

The drawings illustrate the design and utility of the disclosed embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DETAILED DESCRIPTION

Figure 1:
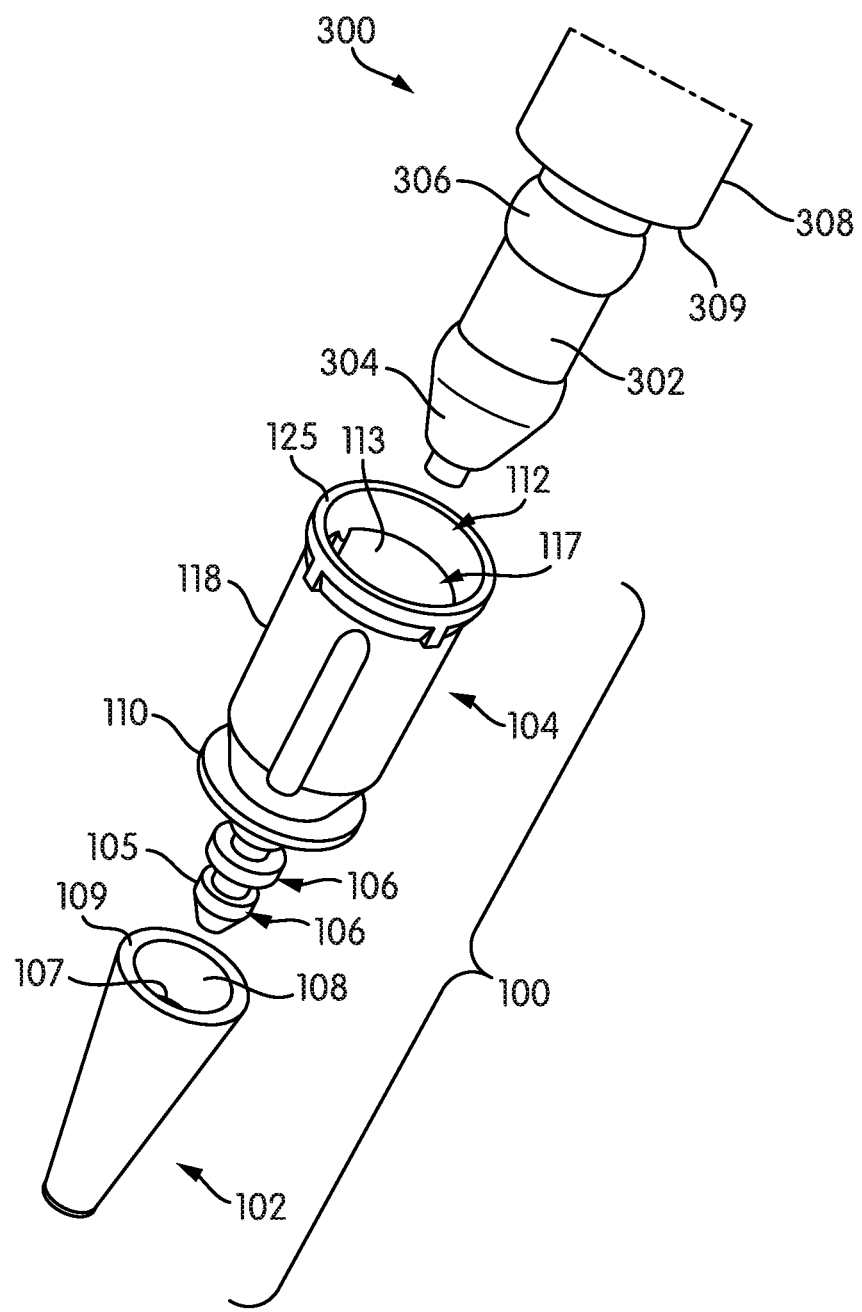
FIG. 1 is an exploded perspective view of an exemplary cleaning member constructed according to embodiments disclosed herein, and further illustrating the working end ("disposable tip interface") of an automated transport mechanism that detachably couples with a proximal portion of the cleaning member.

Before the present systems, methods, and apparatuses are described, it is to be understood that this disclosure is not limited to particular methods, components and materials described, as such methods, components and materials may vary. It is also to be understood that the terminology used herein is for purposes of describing particular embodiments only, and is not intended to be limiting, since the scope of the present disclosure will be limited only in the appended claims.

Various components and sub-assemblies of embodiments of exemplary sample testing systems will now be described in conjunction with the accompanying figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the disclosed embodiments or as a limitation on the scope of the disclosure, which is defined only by the appended claims and their equivalents. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skilled in the art would consider equivalent to the recited value (i.e., having the same function or result). In many instances, the term "about" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. Thus, for example, references to "the method" includes one or more methods, and/or steps of the type described herein, which will become apparent to those persons skilled in the art upon reading this disclosure and so forth. As used in this specification and the appended claims, the term "or" is generally employed in its sense including "and/or" unless the content clearly dictates otherwise.

The term "comprising," which is used interchangeably with "including," "containing," "having," or "characterized by," is inclusive or open-ended language and does not preclude or exclude possible additional elements or acts. The phrase "consisting of" excludes any element, step, or ingredient not specified in the claim. The present disclosure contemplates exemplary embodiments of an apparatus and methods of use thereof corresponding to the scope of each of these phrases. Thus, a system, device or method comprising recited elements or steps contemplates particular embodiments in which the system, device or method consists essentially of or consists of those elements or steps.

Figure 2:
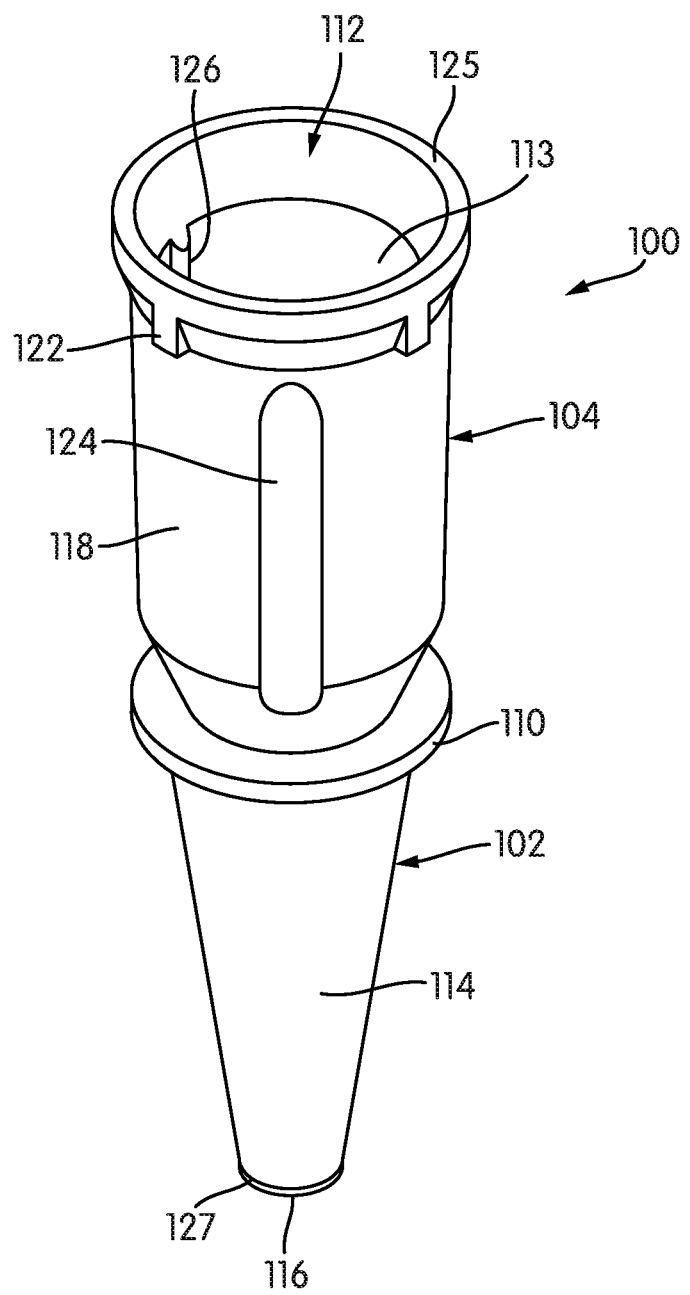
FIG. 2 is a perspective side view of the cleaning member of FIG. 1, when assembled or as molded.
Figure 3:
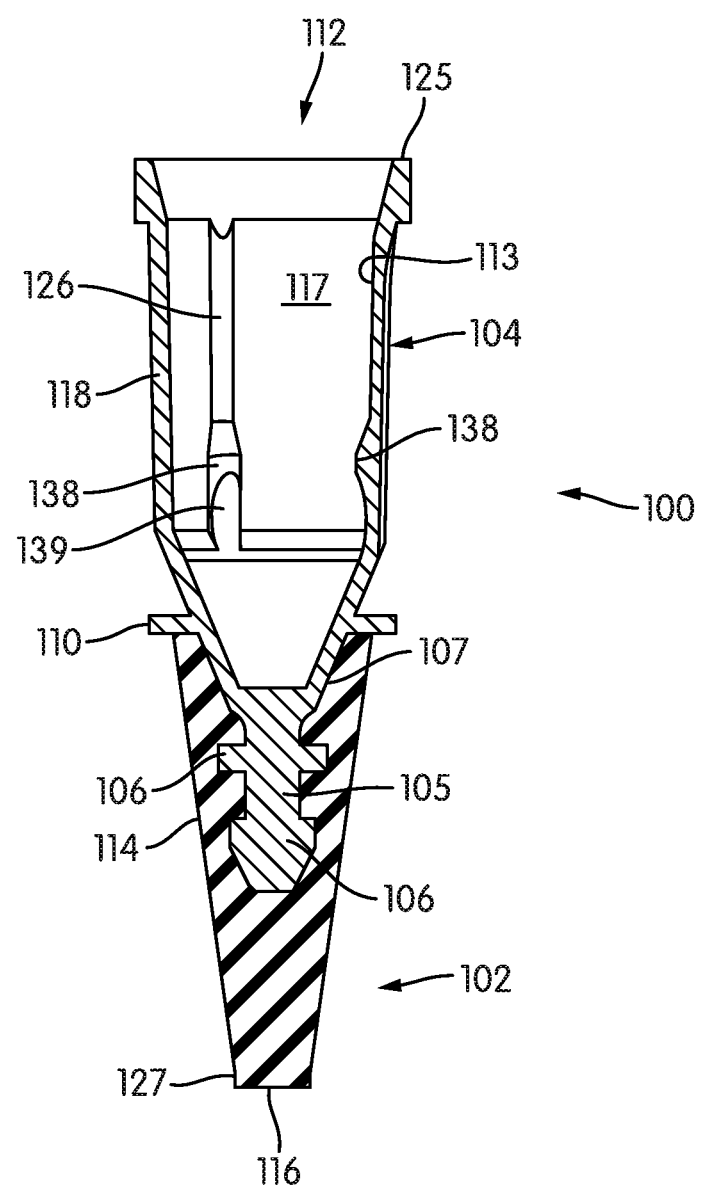
FIG. 3 is a cross-sectional side view of the fully assembled or molded cleaning member of FIG. 1, showing co-molding or an interference fit that joins a proximal coupling element with a distal cleaning element of the cleaning member.

FIGS. 1-3 depict an exemplary cleaning member 100 for use in a sample testing system, according to embodiments disclosed herein. The cleaning member 100 includes a distal cleaning element 102 and a proximal coupling element 104. As described below in greater detail, the respective cleaning and coupling elements 102 and 104 may be manufactured (e.g., molded) as separate components as depicted in FIG. 1, and subsequently joined together, as depicted in FIGS. 2 and 3. Towards this end, the coupling element 104 has a distally projecting extension member 105 including a plurality of radially extending protuberances 106. The extension member 105 and protuberances 106 are dimensioned to form an interference fit with a complementary-dimensioned interior cavity 107 of the cleaning element 102, which is accessed through a proximal end opening 108 thereof. The material(s) used to make the cleaning element 102 and/or coupling element 104 are thus preferably sufficiently compliant relative to each other so that the coupling element 104 is fixedly-joined to the cleaning element 102 by inserting the extension member 105 through opening 108, until the extension member 105 (including the protuberances 106) makes a "snap-fit" connection within the cavity 107. A radially outward ring 110 disposed on the coupling element 104 butts against a rim 109 surrounding the proximal opening 108 to prevent over-insertion of the extension member 105 into cavity 107. It will be appreciated that alternative attachment mechanisms and configurations may be used to join together the cleaning and coupling elements 102 and 104, such as a frictional fit, a weld, or an adhesive.

The respective cleaning and coupling elements 102 and 104 may be joined together prior to providing the (assembled) cleaning member 100 for use in a sample testing system, or alternatively the cleaning and coupling elements 102 and 104 may be provided as separate components that are joined together by the system at the time of using the cleaning member 100. By way of example, a system testing system may include a first structure that holds one or more cleaning elements 102, and a second structure that supports or holds one or more coupling elements 104. At the time of use, a working end of an automated transport arm engages (i.e., detachably couples with) a coupling element 104 held in the second support structure, and transports the detachably-coupled coupling element 104 to a location proximate a cleaning element 102 held in the first support structure. The automated arm maneuvers the coupling element 104 to insert the extension member 105 thereof through the open proximal end 108 and interior cavity 107, respectively, of the cleaning element 102, to thereby form an interference fit to join the coupling element 104 to the respective cleaning element 102. The fully assembled cleaning member 100 is then ready to use and already coupled to the automated transport arm. The cleaning elements 102 in the foregoing example may be environmentally sealed prior to use, e.g., in individually sealed receptacles, or in a sealed tray, in which a frangible member forming the respective seal is penetrated by the extension member 105, as the coupling element 104 engages the cleaning element 102.

Alternatively, the cleaning member 100 may be manufactured as an integral unit, e.g., in which the respective cleaning and coupling elements 102 and 104 are formed in their joined configuration using a co-molding process. In such embodiments, such as the below-described embodiments shown in FIGS. 9-14, it may still be desirable to environmentally seal the cleaning member(s) 100 prior to use, e.g., in individually sealed receptacles, or in a sealed tray, in which a frangible member forming the respective seal is penetrated by the working end of the automated transport arm as it engages the proximal end of the coupling element 104 of the cleaning member 100.

By way of illustration and with specific reference to FIG. 1, a proximal body portion 118 of the coupling element 104 forms an elongated, funnel-shaped interior recess 117 that is accessed through the open proximal end 112 of the coupling element 104. The open end 112 of the coupling element 104 is bordered by a rim 125 having an axially facing surface. The recess 117 (best seen in FIGS. 3, 4 and 5) is dimensioned to receive and releasably engage (mate) with the working end ("disposable tip interface" or "DiTi") 302 of an automated transport arm 300. In particular, radially enlarged protrusions 304 and 306 disposed on the DiTi 302 form a frictional fit with an interior surface 113 of the interior recess 117 to thereby detachably-couple the DiTi 302 with the coupling element 104 when the DiTi 302 is inserted through the open end 112 thereof. The detachably-coupled components 102 and 104 may thereafter be de-coupled (i.e., detached) by action of a sleeve 308 that moves relative to the DiTi 302 by one or both of advancement of the sleeve 308 over the DiTi 302, or by withdrawal of the DiTi 302 into the sleeve 308, until a distal end 309 of the sleeve 308 contacts and engages the proximal rim 125 of the coupling element 104 to dislodge the coupling element 104 from the DiTi 302.

As best seen in FIG. 3, a plurality of longitudinally oriented linear ribs 126 are formed on the interior surface 113 of the coupling element 104. While there are three linear ribs 126 depicted in the illustrated embodiments, alternative embodiments may have a fewer (i.e., 1 or 2) or greater (i.e., 4 or more) amount of linear ribs 126 on the interior surface 113. In further alternative embodiments, no linear ribs 126 are provided on the interior surface 113, and the ribs 126 in the depicted embodiments should be considered optional. In embodiments having at least two linear ribs 126, the ribs 126 are preferably spaced substantially equal distances apart from one another on the interior surface 113. Accordingly, in the illustrated embodiments, the three ribs 126 are spaced approximately one hundred twenty degrees apart from each other on the interior surface 113. The ribs 126 each protrude inward into recess 117 along their length, thereby decreasing the inner fitment diameter of the recess 117 to facilitate engagement of the DiTi protuberances 304 and 306 to the coupling element 104. The ribs 126 may be beveled at an upper, or proximal, end thereof or otherwise preferably dimensioned to at least partially deform as the DiTi protuberances 304 and 306 are inserted into the recess 117. In some embodiments, the amount of protrusion of the ribs 126 may gradually increase in size as the respective ribs approach the bottom of the recess 117 within the coupling member 104. In the illustrated embodiments, the thickness of the ribs is increased at a radial-inward apex 138 within the recess 117, and thereafter reduced, wherein a bottom portion 139 of each rib 126 is recessed to accommodate the frictional engaging protuberance 304 on the DiTi 302. Alternatively, or in addition thereto, in certain embodiments, the linear ribs 126 may gradually increase in overall thickness as they approach the bottom of the recess. Thus, a gradual increase in thickness and/or radial geometry is contemplated for the gradual tapering of the one or more linear ribs 126, which additionally serves to center the DiTi 302 as it is inserted through open end 112 of the coupling element 104, and into recess 117.

One or more longitudinal indentations, or recesses 124, are disposed on, and extend along at least part of the length of, the exterior surface 118 of the coupling element 104. The recesses 124 may be formed in any shape such as, for example, concave, notched, squared, etc. In various embodiments, the length of each of the one or more recesses 124 is aligned with (i.e., in direct opposition), and is approximately the same length as, a corresponding linear rib 560 disposed on the interior surface 113. Thus, the illustrated embodiment has three exterior linear recesses for a one-to-one relationship with the respective three linear ribs 126 on the interior surface 113. The coupling of an interior surface linear rib 126 with an exterior surface recess 124 enhances the predictability of the frictional attachment of the coupling element 104 with the DiTi 302 of the automated transport arm 300. In particular, as the DiTi 302 of the transport arm 300 is lowered into the recess 117 of the coupling element 104, the distal end protuberances 304 and 306 of the DiTi 302 contact and press against the linear ribs 126, thereby causing the coupling element 104, and in particular the one or more recesses 124, to flex and/or expand radially outward with respect to the axial center thereof to accommodate the DiTi 302 and enhance its frictional attachment or "mating" of the transport arm 300 with the coupling element 104.

A plurality of protrusions 122 extend radially outward from proximal rim 125 surrounding the proximal end opening 112 of the coupling element 104. The protrusions 122 are preferably substantially equal distances apart from one another on the rim 125, and facilitate stacking and/or docking of the coupling elements 104 (as separate components) and/or the fully assembled cleaning members 100 within a well of a multi-well tray for use in an automated sample testing system (as described herein).

The coupling element 104 may be molded from a number of different polymer and heteropolymer resins, including, but not limited to, polyolefins (e.g., high density polyethylene ("HDPE"), low density polyethylene ("LDPE"), a mixture of HDPE and LDPE, or polypropylene), polystyrene, high impact polystyrene and polycarbonate. Although LDPE is a softer, more malleable material than HDPE, the softness of LDPE provides greater flexibility in the distally projecting extension member 105 and protuberances 106, for securably engaging the cleaning element 102 within the cavity 107. Such added flexibility may also facilitate the frictional engagement of the working end 302 of the transport arm 300 within the proximal interior cavity 117 of the coupling element 104. In a presently preferred embodiment, the coupling element 104 is formed out of polypropylene ("PP"). Regardless of the type or mixture of the respective chosen materials, the cleaning element 102 and the coupling element 104 are preferably made using a known molding process, such as by injection, compression, transfer or RTV molding. The elements 102 and 104 may be molded as separate components that are later joined together, or as a single component manufactured using a known co-molding (or "over-molding") process in which the cleaning element 102 is molded onto the extension member 105 of the coupling member 104, so that the two components are joined together in the manufacturing process.

The cleaning element 102 has a uni-body construction that may be formed using a known injection molding process. The materials used in the molding process should be oil free and any mold-release agents used during the molding process are preferably limited to ones that do not leave an oily residue on the surface 114 of the cleaning element 102. In various embodiments, one or more cleaning elements 102 may be made out of an adhesive material, such as (without limitation) silicone, platinum cured silicone, thermoplastic polyurethane, thermoplastic elastomer, thermoplastic rubber, or a gel. A preferred adhesive material is one that is tacky, but does not leave a residue on surfaces which it contacts.

Alternatively or additionally, one or more cleaning elements 102 may be made out of a material that generates a static attraction to particulates and/or other materials that can interfere with the transmission by the optical element of electromagnetic radiation emitted or reflected by the sample, such as (without limitation) silicon, polyvinyl chloride, polypropylene, polyethylene, polyurethane, polyester or polystyrene. Notably, some of the foregoing materials that are adhesive also generate a static attraction to unwanted debris.

Alternatively or additionally, one or more cleaning elements 102 may be made out of an absorbent material capable of retaining a fluid cleaning and/or sterilizing substance, and of applying the retained fluid to the surface of the respective structure being cleaned and/or sterilized. Such absorbent materials include but are not limited to hydrophilic materials, and may also include hydrophobic materials such as PP and other plastics. Additional examples of absorbent materials that may be used for forming the cleaning element 102 include, without limitation, porous plastic materials in a sponge or foam form made of materials such as PP, HDPE, LDPE, polytetrafluoroethylene ("PTFE"), polyvinylidene fluoride ("PVDF"), ethylene vinyl acetate ("EVA"), Porex® polymers, cellulose fibers (such as cotton fabric or cloth), and polymicro fibers. Exemplary fluid cleaning and/or sterilizing substances that may be used include, without limitation, isopropyl alcohol, ethyl alcohol, diluted hydrochloric acid (e.g., 20% solution), oxalic acid, diluted sodium hydroxide (e.g., 50% solution), and diluted sodium hypochlorite (e.g., 15% solution). A preferred cleaning and/or sterilizing fluid should be a composition that is easily removed (e.g., by reabsorption or evaporation), and should not leave a residue on the respective optical element after contact. Certain fluids should not be used, such as window cleaning fluids with ammonia, gasoline, denatured alcohol, carbon tetrachloride and or acetone, since such fluids may damage the respective optical element and/or sample test receptacle well. The cleaning and/or sterilizing fluid is kept in a separate receptacle from the absorbent cleaning elements 102, which are at least partially inserted into the cleaning and/or sterilizing fluid at the time of use. Alternatively, the absorbent cleaning elements 102 may be pre-soaked with the cleaning and/or sterilizing fluid prior to being supplied for use.

In various embodiments, the cleaning element 102 may have different shapes, dimensions and configurations as best suited for performing the cleaning and/or sterilizing functions of the sample testing system in which it is used. For example, cleaning elements 102 of selected cleaning members 100 may be specially shaped and/or dimensioned for reaching and cleaning and/or sterilizing particular types of optical elements, test receptacle wells, and other components of a sample testing system in which they are used. The distal end 116 of the cleaning element 102 may be flat or curved, and preferably is at least somewhat compressible to avoid damaging components of the test system during the cleaning process.

In some embodiments, a sample testing system may be provided with multiple types of cleaning members 100, including one or more cleaning members 100 having cleaning elements 102 made of a first (e.g., adhesive) material, and one or more additional cleaning members 100 having cleaning elements 102 made of a second (e.g., absorbent) material. For example, a sample test system may be provided with a one or more cleaning members 100 having adhesive cleaning elements 102, and one or more cleaning members 100 having absorbent cleaning elements 102 that retain a cleaning and/or sterilizing fluid, wherein a cleaning member 100 having an adhesive cleaning element 102 is used to perform an initial cleaning of one or more optical elements, and a cleaning member 100 having a fluid-retaining cleaning element 102 is thereafter used to perform a secondary (i.e., finishing") cleaning of the same one or more optical elements.

Figure 4:
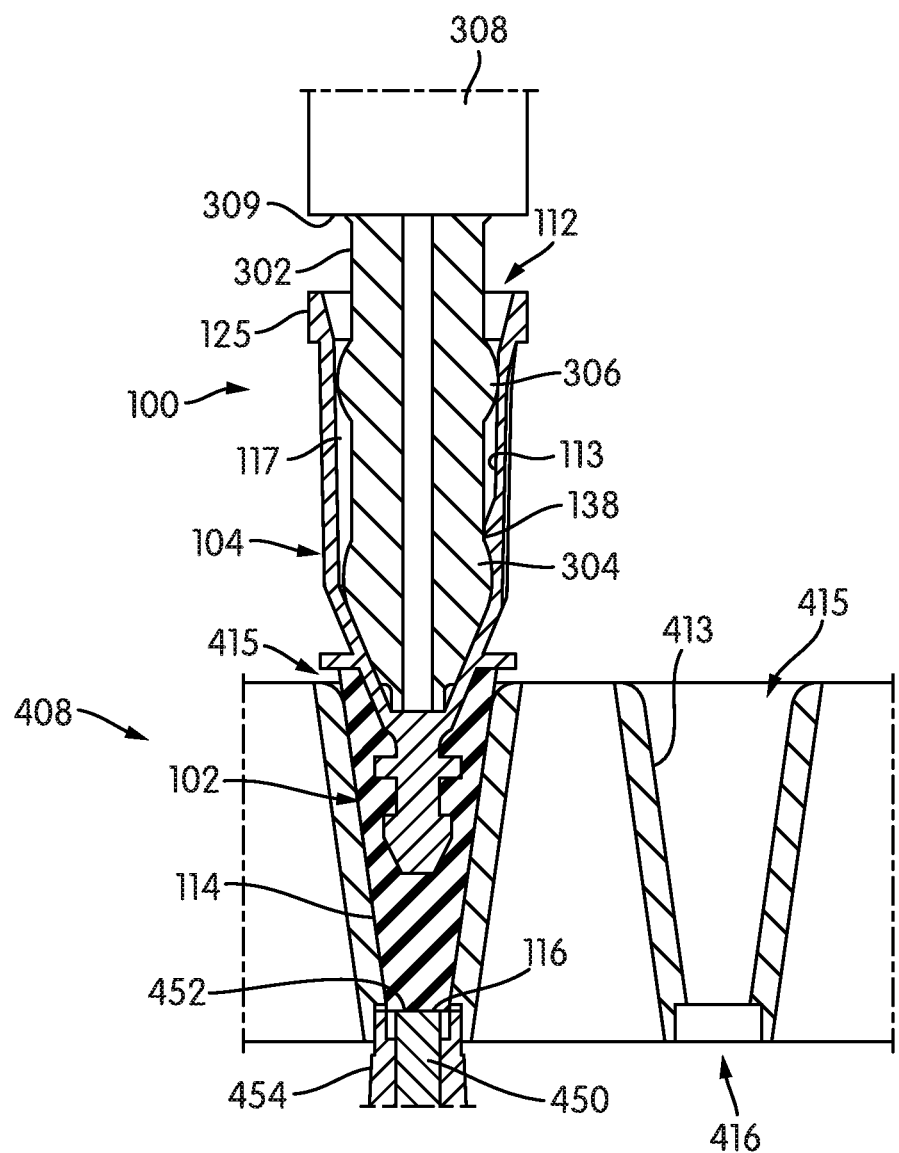
FIGS. 4 and 5 are respective cross-sectional side elevation and cross-sectional side perspective views of the disposable tip interface of FIG. 1, inserting a detachably-coupled cleaning member into a test receptacle well of a test receptacle holder, wherein a distal tip of the cleaning member contacts an upward, axial facing end of an optical fiber positioned proximate to an open bottom portion of the test receptacle well.
Figure 5:
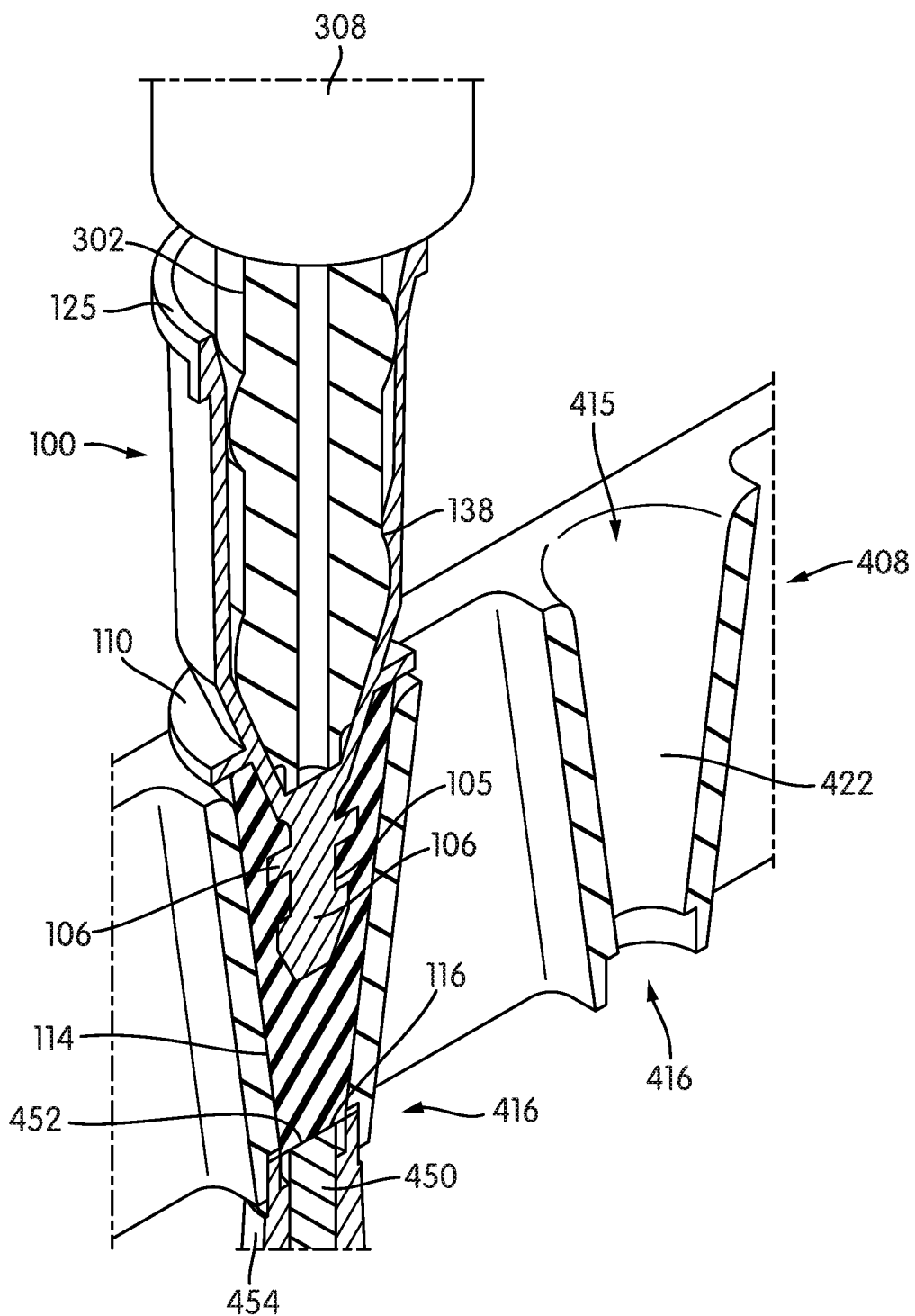

FIGS. 4 and 5 are respective cross-sectional side elevation and cross-sectional side perspective views of the DiTi 302 of the automated transport arm 300 inserting an already detachably-coupled cleaning member 100 into a test receptacle well 415 of a test receptacle holder 408 positioned on a processing deck of a sample testing system (described below in greater detail), wherein the distal end surface 116 of the cleaning element 102 contacts an upward axial facing end surface 452 of an optical fiber 450 surrounded by a sleeve 454, positioned proximate to an open bottom portion 416 of the test receptacle well 415. By way of non-limiting example, the test receptacle holder 408 comprises a plurality of test receptacle wells 415 (two adjacent wells 415 or shown in FIGS. 4 and 5), and the sample testing system may be provided with a plurality of similar test receptacle holders 408, each having a plurality of test receptacle wells 415. It should be appreciated that, in alternate embodiments of sample testing systems, a test receptacle holder may have a different construct, for example, a platform for holding a microtiter plate.

The automated transport arm 300, and the DiTi 302 in particular, are configured to detachably couple a fully assembled cleaning member 100 located in a cleaning member well of a nearby cleaning member holder, (such as cleaning member well 426 of the cleaning member storage tray 424 shown in FIGS. 9-14, described below), or to otherwise first detachably couple a coupling element 104 located in a coupling element holder (not shown) and thereafter join a cleaning element 102 located in a separate (e.g., environmentally sealed) cleaning element holder (also not shown) to the already detachably-coupled coupling element 104 to thereby have a detachably-coupled cleaning member 100. In either case, the transport arm 300 maneuvers the DiTi 302 to insert the detachably-coupled cleaning member 100 into the test receptacle well 415, as shown in FIGS. 4 and 5, such that a distal tip 116 of the cleaning element 102 is contacting (to thereby clean and/or sterilize) the axial facing distal end 452 of an optical fiber 450 positioned proximate to the open bottom end 416 of the test receptacle well 415. It should be appreciated that it is not necessarily required for the distal tip 116 of the cleaning element 102 to make physical contact with the axial facing end 452 of the optical fiber 450, for example, if the cleaning element 102 comprises a material that generates a static attraction to clean the optical fiber end 452, as described above.

It should be appreciated that optical fiber 450 can be one of a plurality of optical fibers (not shown in the Figures) employed by the sample testing system to conduct optical interrogation of samples contained in test receptacles seated in the respective test receptacle wells 415. In particular, the optical fiber(s) 450 transmit electromagnetic radiation (which may or may not be in the visible light spectrum) that is emitted and/or reflected by the sample, as is explained in detail in the above-incorporated patent applications. It should be appreciated that optical elements other than optical fibers may be used for this purpose in alternate sample testing systems, and in particular other optical elements having a protective surface, such as (without limitation) a fluorometer comprised of fixed lenses and filters, a photomultiplier tube ("PMT"), and/or other optical elements used in the field of biological sample testing, such as a lens, window, mirror, reflector, filter, film, and/or the like disposed between the sample and an illuminator (e.g., lasers, LEDs, tungsten, halogen, mercury arc, xenon arc, metal halide lamps) or detector (PMT, CCD, CMOS, photodiodes, photodiode array). Regardless of the type of optical element(s) that may be employed by a sample testing system, it is critical that the optical pathway extending between, and including, the end surfaces of the respective optical element and test receptacle be free and clear of any debris that may interfere with the optical interrogation process. Thus, the cleaning members 100 of various embodiments may be suitably modified to accommodate the cleaning and/or sterilizing alternative types of optical elements and/or test receptacle configurations that may be employed in various sample testing systems.

Although practice of the disclosed embodiments is not limited to the cleaning element 102 having any particular shape or dimensions, in the illustrated embodiment, the outer surface 114 of the cleaning element 102 and the interior surface 413 of the test receptacle well 415 have complementary, generally frustoconical shapes. In this manner, the cleaning element 102 advantageously contacts to clean and/or sterilize the interior surface 413 of the test receptacle well 415 at the same time that the distal end 416 of the cleaning element 102 contacts to clean and/or sterilize the end surface 452 of the optical fiber 450.

Figure 6:
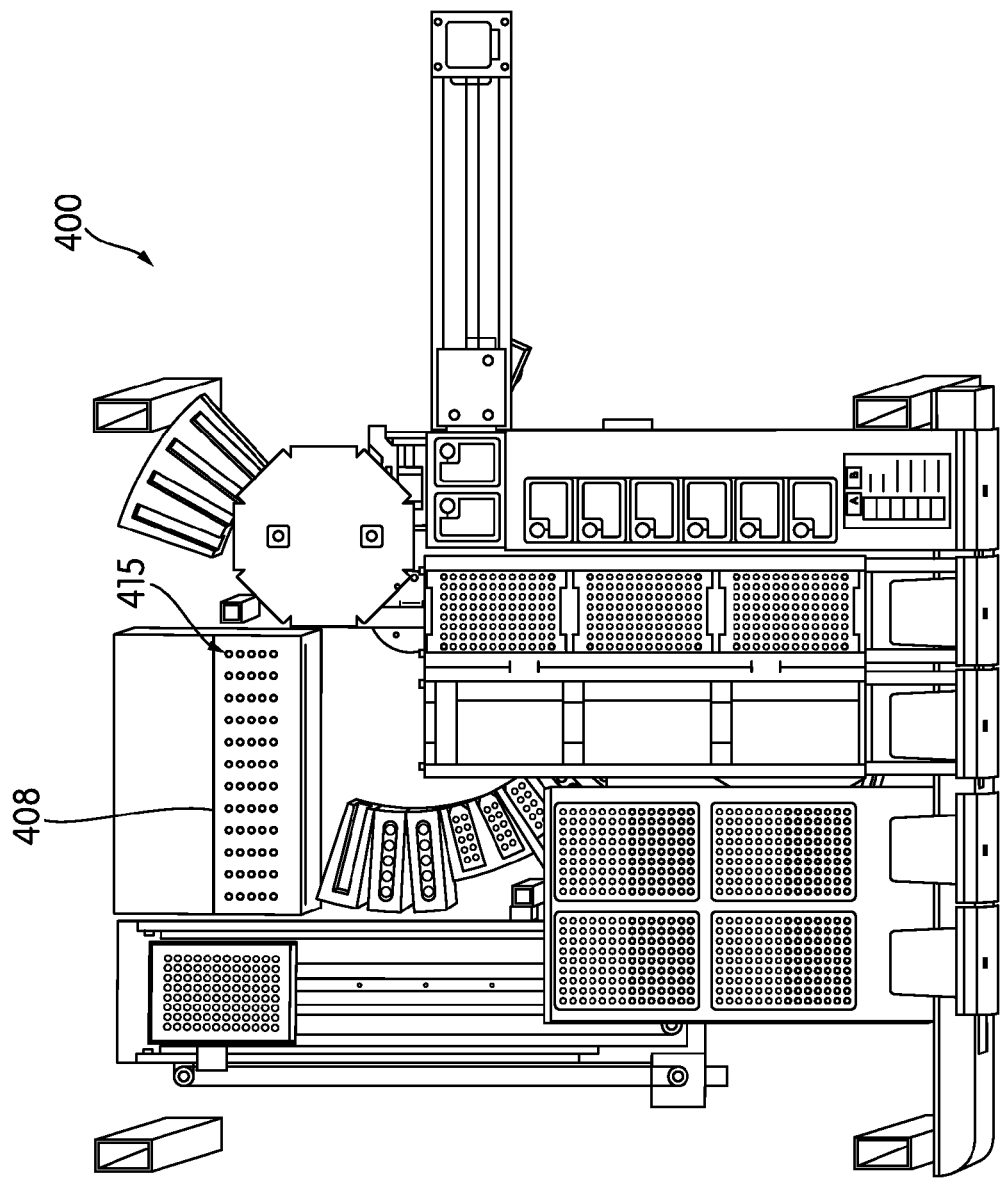
FIG. 6 is a top plan view of an exemplary sample processing instrument deck of an automated sample testing system.

FIG. 6 depicts one embodiment of a sample processing instrument deck 400 of a sample testing system, in which an automated transport arm assembly (such as the below-described automated transport arm gantry 402 and associated transport arms 410 and 418 shown in FIGS. 7 and 8) is omitted for clarity. The sample processing instrument deck 400 includes a dozen test receptacle holders 408, each holder 408 having five test receptacle wells 415, for a total of sixty test receptacle wells 415. The individual receptacle holders 408 are best seen in the partial perspective view of an alternate embodiment sample processing instrument deck 400' depicted in (below-described) FIG. 14. Reference is made to the above-incorporated U.S. application Ser. No. 14/213,900, which discloses additional details of an exemplary sample processing instrument deck, and of the operation of an exemplary sample testing system of which the instrument deck is a part.

Figure 7:
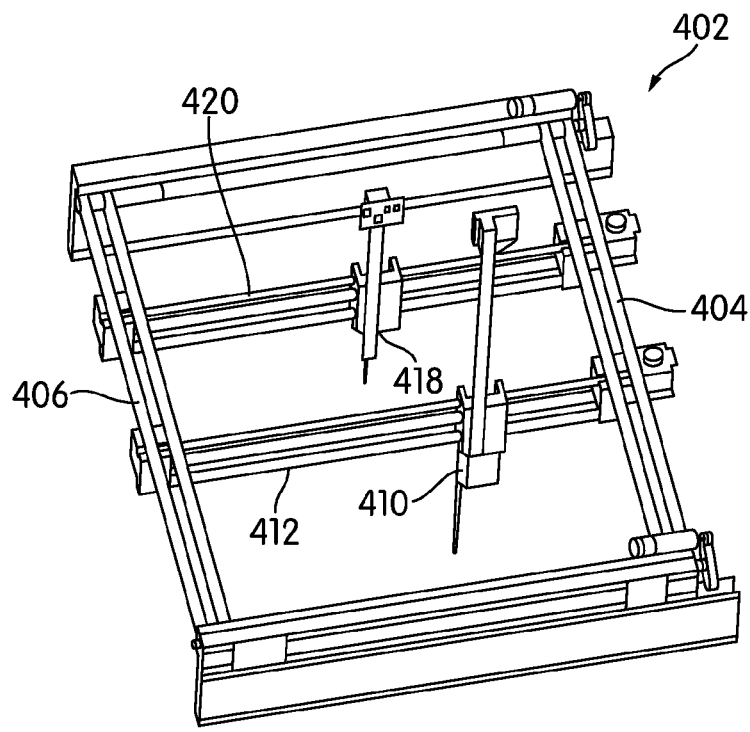
FIG. 7 is a perspective view of an automated transport gantry for use with the sample processing instrument deck of FIG. 6.
Figure 8:
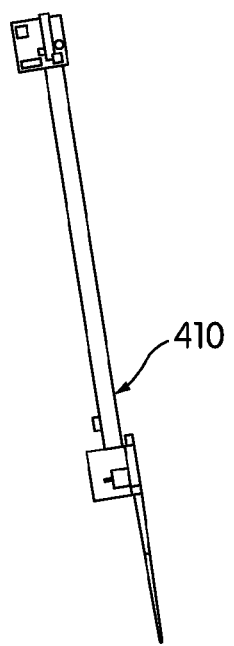
FIG. 8 is a perspective view of a transport arm of the transport gantry of FIG. 7.
Figure 9:
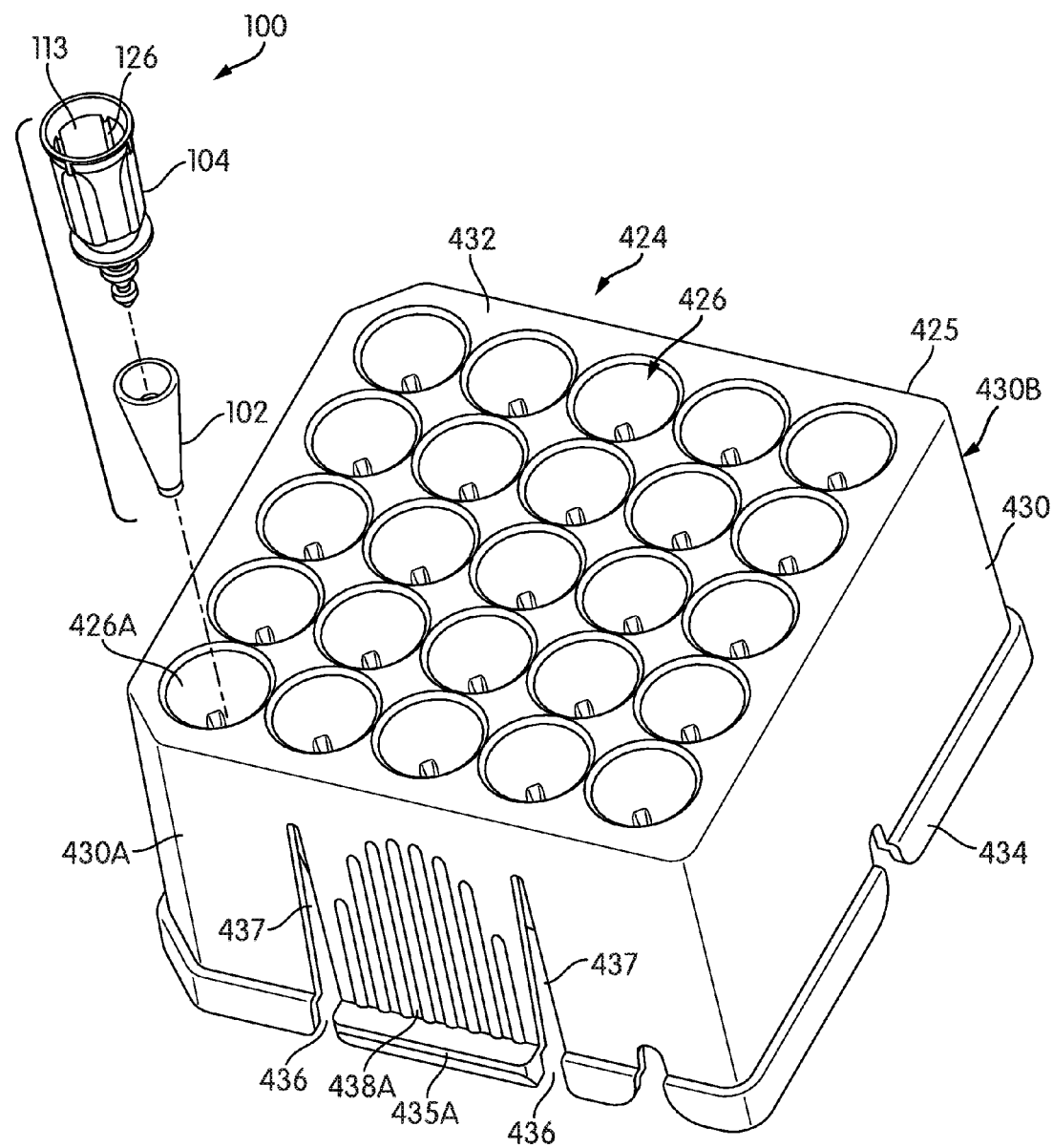
FIG. 9 is a perspective view of an exemplary cleaning member storage tray constructed according to embodiments disclosed herein, and further illustrating an exploded perspective view of an exemplary cleaning member seated in a corner cleaning member well of the storage tray.

FIG. 7 depicts an exemplary automated transport system gantry 402, including a pair of transport arms 410 and 418 (transport arm 410 is also shown in FIG. 8). The transport system gantry 402 can be employed in embodiments of a sample processing instrument deck, including embodiments incorporating and using the cleaning members 100 disclosed herein (such as instrument deck 400' of below-described FIG. 14). While the depicted transport arms 410 and 418 are different in appearance from the automated transport arm 300 (including the DiTi interface and sleeve 302/308) depicted in FIGS. 1, 4 and 5, the operation and functionality of the transport arms 410, 418 is substantially the same as for transport arm 300. Thus, the transport system gantry 402, including transport arms 410 and 418, is illustrated and described herein for purposes of better understanding the operation of the automated transport arm 300 and DiTi/sleeve 302/308 depicted in the above-described embodiments of FIGS. 1-5.

Figure 14:
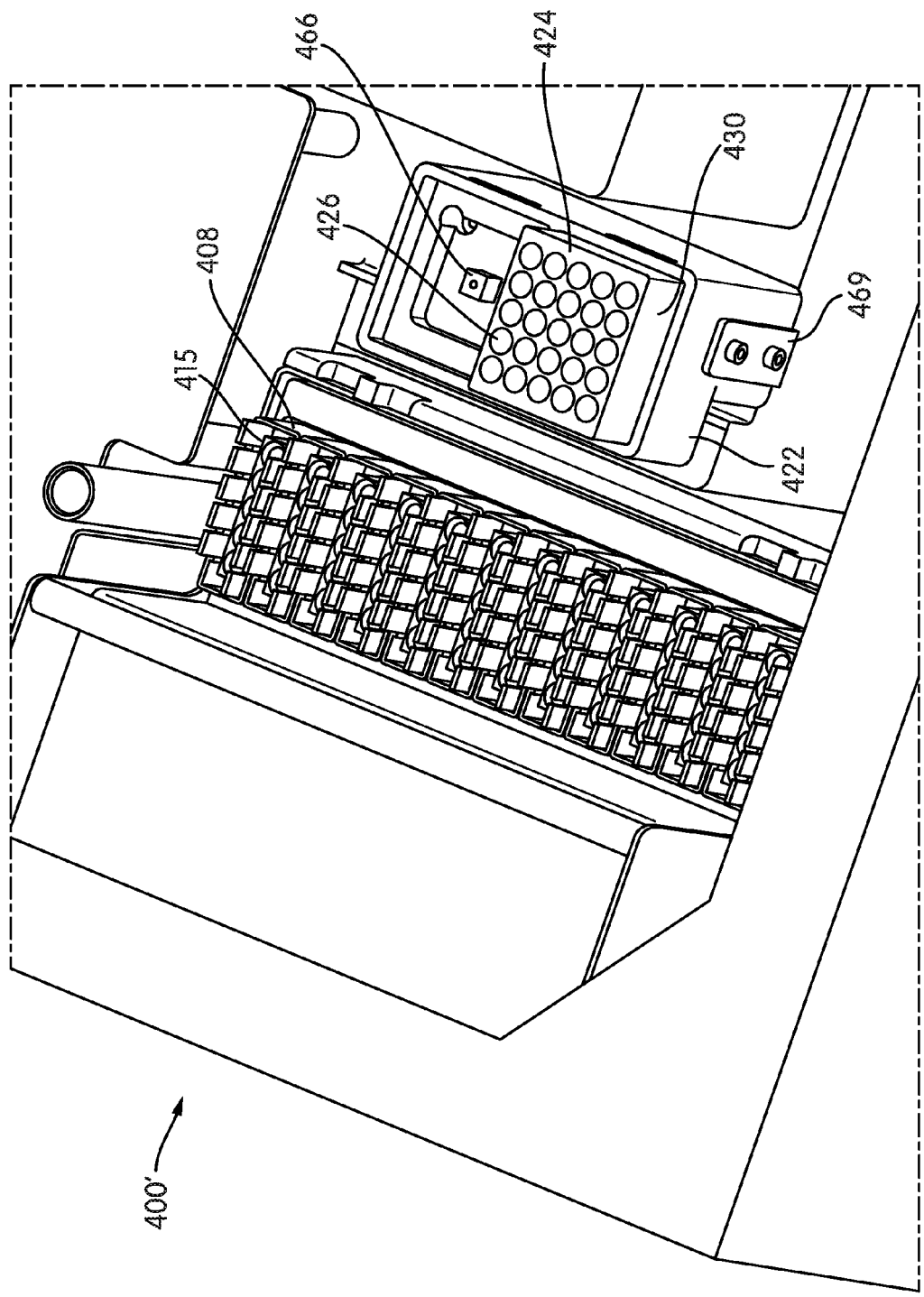
FIG. 14 is a perspective view of a portion of a sample processing instrument deck, with the cleaning member storage tray holder of FIG. 13 installed thereon.

Transport arms 410 and 418 may be used for detachably coupling and transporting objects, such as the cleaning members 100, along two axes (i.e., X and Y) in order to position the detachably-coupled objects at respective targeted locations of a sample processing instrument deck (e.g., instrument deck 400' of FIG. 14). In particular, the transport system gantry 402 can be used for detachably coupling, moving, inserting, and detaching the cleaning members 100, as described above with respect to the transport arm 300 of the embodiments of FIGS. 1-5. Towards this end, transport arm 410 is movable along a first X axis rail 412, and transport arm 418 is movable along a second X axis rail 420. The X axis rails 412 and 420 are, in turn, both movable along a pair of Y axis rails 404 and 406. In this manner, the respective X rails 412 and 420, and Y axis rails 404 and 406, collectively facilitate movement of the transport arms 410 and 418 in order to position the respective arms above respective targeted objects to be detachably coupled and moved to targeted locations for positioning (e.g., inserting) and (optionally) decoupling the detachably-coupled objects. The transport arms 410 and 418 are configured to move vertically (i.e., along their "Z axis") for lowering or raising a respective detachably coupled object, e.g., for inserting a detachably-coupled cleaning member 100, relative to a targeted object underlying the respective arm. A controller (not shown) is configured to control operation of, inter alia, the transport system gantry 402, including arms 410 and 418.

In alternate embodiments, an automated transport arm for use in the disclosed embodiments herein may be an articulating (e.g., robotic) arm that pivots about a fixed base, although this is not necessary for practicing the disclosed embodiments.

Figure 10:
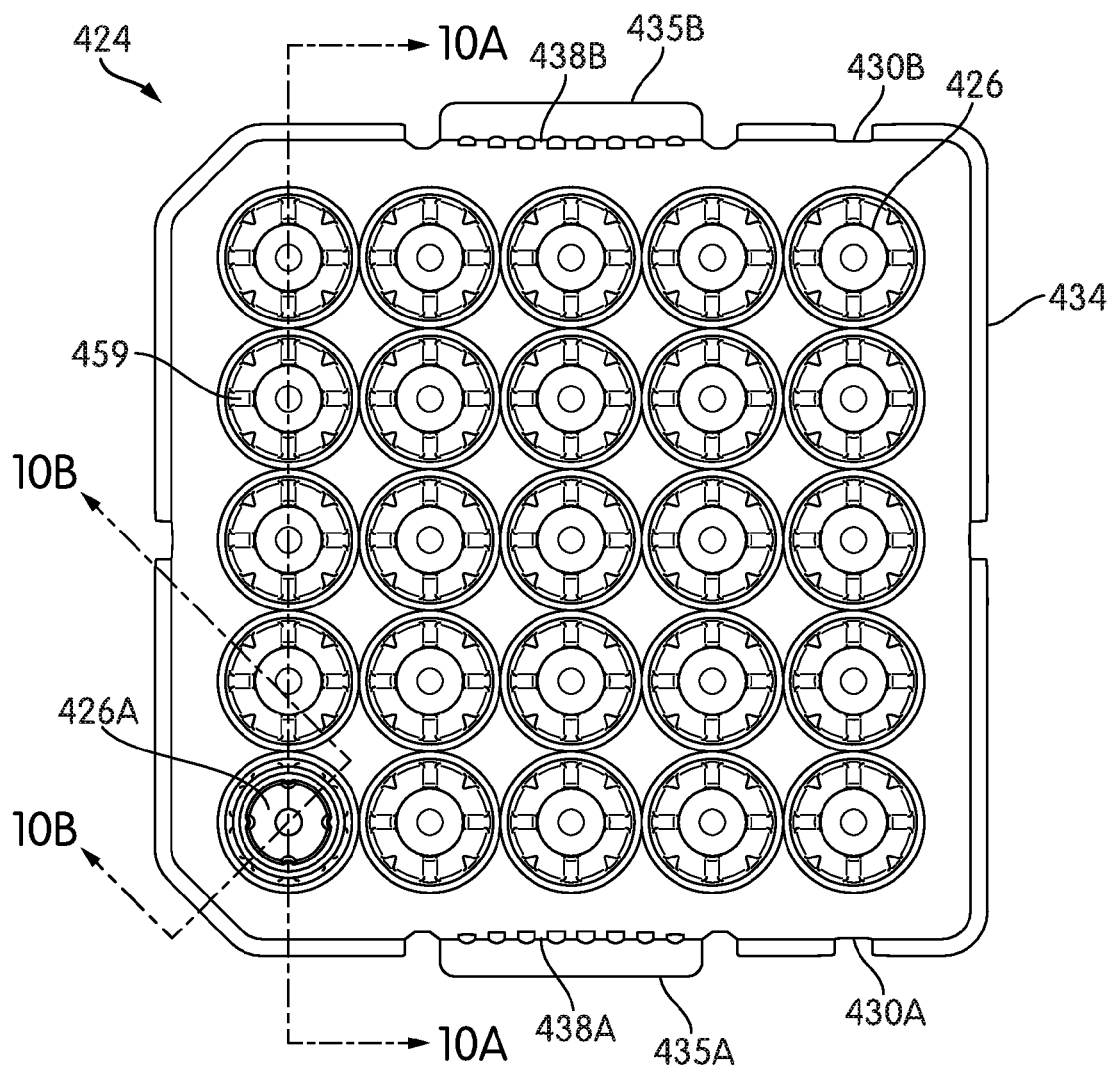
FIG. 10 is a top view of the cleaning member storage tray of FIG. 9, including the seated cleaning member.

FIGS. 9-12 depict an exemplary cleaning member storage tray 424 comprising a uni-body structure 425 that is molded out of a same or similar plastic material used to form the cleaning member coupling element 104, although other suitable materials and manufacturing techniques may be used for making the cleaning member storage tray 424. The storage tray body 425 defines a five-by-five array (i.e., twenty-five total) inwardly recessed cleaning member wells 426. The storage tray body 425 has a box-like outer shape, including four continuous sidewalls 430 that meet at a top surface 432 in which the respective openings of the cleaning member wells 426 are disposed. An outwardly protruding lip 434 substantially circumscribes a bottom end portion of the four sidewalls 430, as best seen in FIG. 10. Opposing side walls 430A and 430B of the storage tray body 425 have a pair of laterally spaced apart slots 437 extending from respective openings 436 in the bottom lip 434 of the sidewall 430A, 430B upward to an apex, the slots 437 defining flexible tabs 438A and 438B in sidewalls 430A and 430B, respectively. The bottom edge of tabs 438A and 438B have respective outwardly extending latching flanges 435A and 435B. The tabs may be flexed into the storage tray body 425 by inwardly depressing the latching flanges 435A and 435B into the storage tray body 425.

An exemplary cleaning member 100 is seated in a respective cleaning member receptacle 426A in a corner of the storage tray 424. For illustration of an alternative embodiment, there are four longitudinally oriented linear ribs 126 formed on the interior surface 113 of the coupling element 104 of the cleaning member of FIGS. 9-12. The linear ribs 126 are spaced substantially equal distances apart from one another on the interior surface 113 of the cleaning member 100 of FIGS. 9-12, and are the same in dimension and features as the linear ribs 126 of cleaning member 100 of FIGS. 1-5.

Figure 10A:
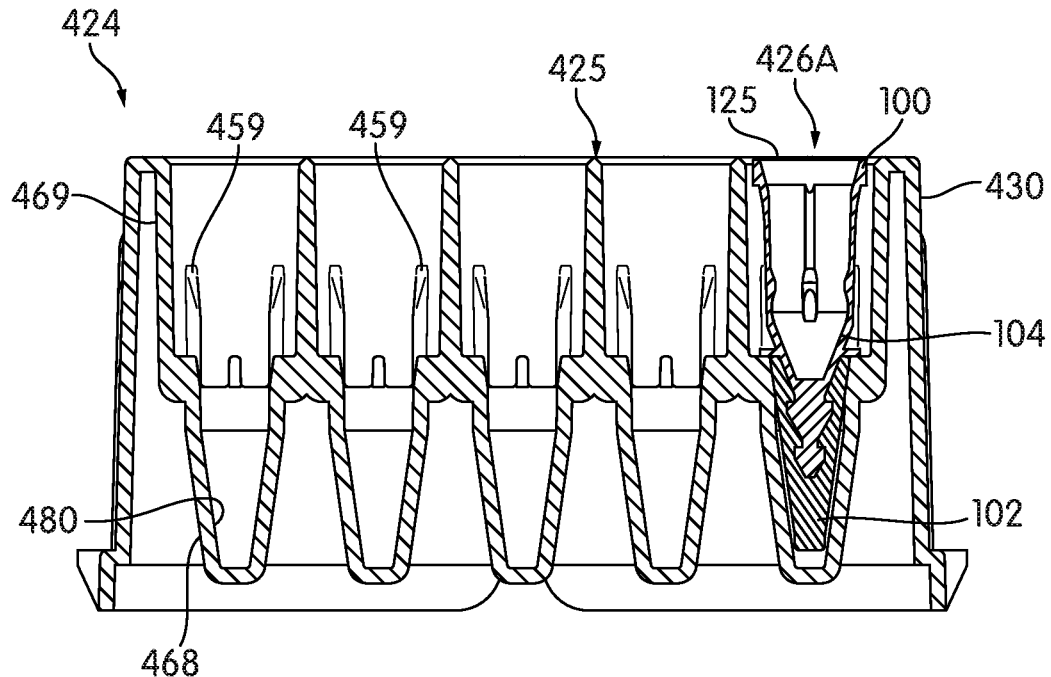
FIG. 10A is a cross-sectional view taken along lines A-A in FIG. 10.
Figure 10B:
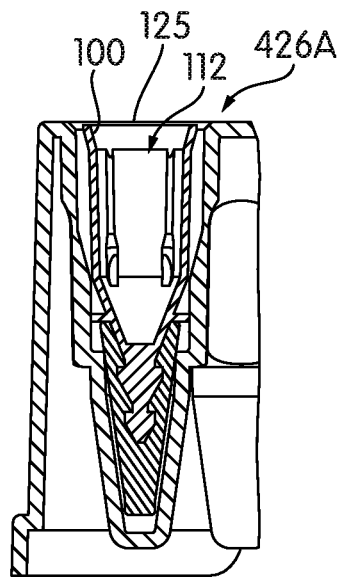
FIG. 10B is a cross-sectional view taken along lines B-B in FIG. 10.

As best seen in FIGS. 10A and 10B, the cleaning member wells 426 of the storage tray 424 include a lower portion 468 having an interior surface 480 configured and dimensioned to snuggly seat the distal cleaning element 102 of the cleaning member 100, and an upper portion 469 having a plurality of spaced apart catch members 459 that receive and support the coupling element 104. The body 425 and respective storage wells 426 of the cleaning member storage tray 424 are dimensioned and configured such the proximal end rim 125 of the cleaning member coupling element 104 is approximately co-extensive with the top surface 432 of the storage tray 424. In this manner, the proximal open end 112 of the cleaning member coupling element 104 is readily accessible for engagement by an automated transport arm, such as the DiTi 302 of transport arm 300 depicted in FIGS. 1, 4 and 5. For ease in illustration, no transport arm is depicted in FIGS. 9-12.

Figure 11A:
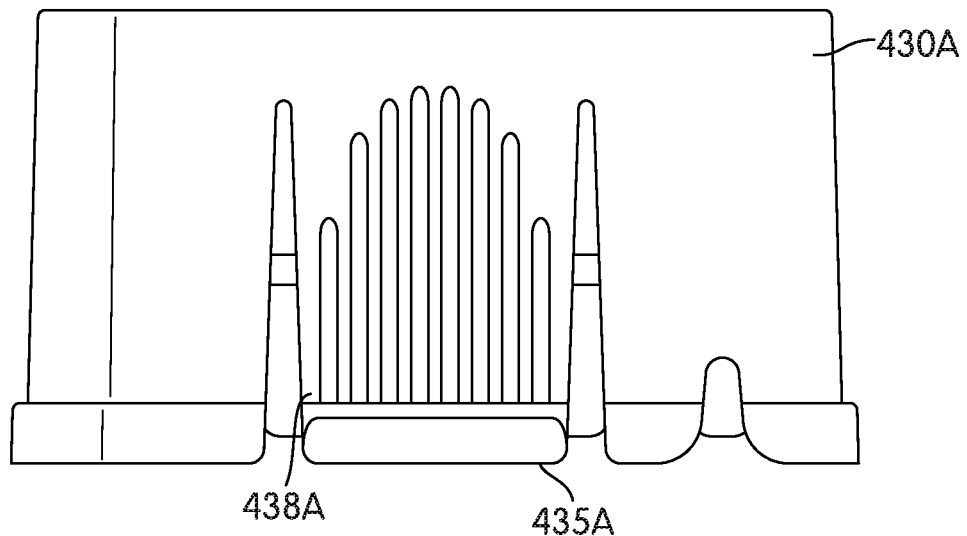
FIGS. 11A and 11B are respective side views of the cleaning member storage tray of FIG. 9.
Figure 11B:
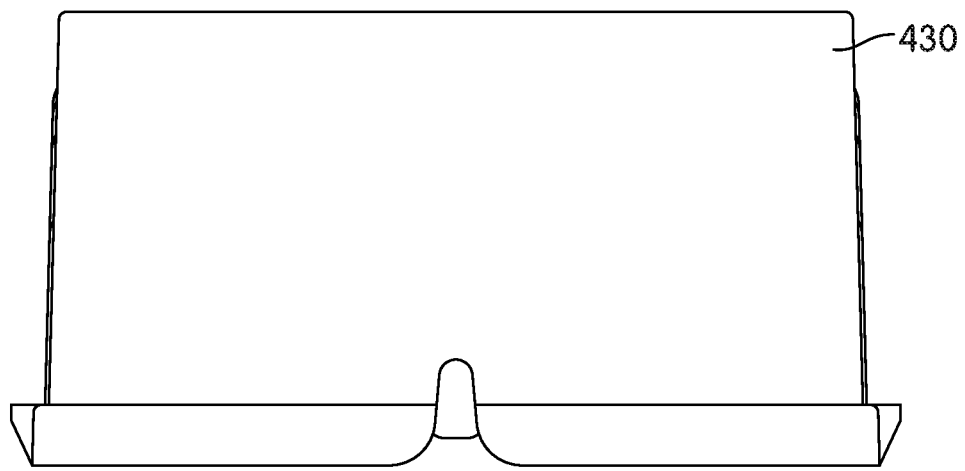
Figure 12:
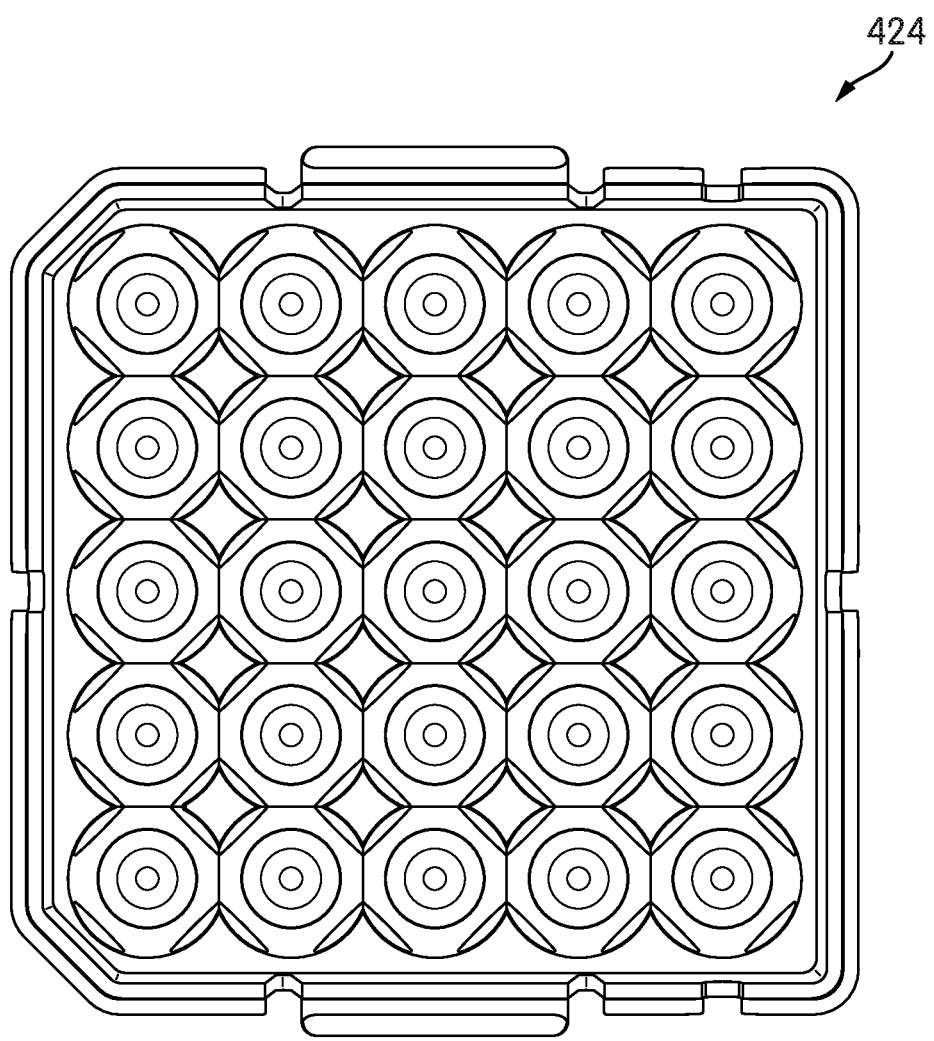
FIG. 12 is a bottom view of the cleaning member storage tray of FIG. 9.

The top surface 432 of the storage tray 424 may (optionally) be substantially environmentally sealed by a frangible sealing member (not shown) that protects and keeps the cleaning elements 102 of the cleaning members 100 in fresh and moist (if appropriate) condition within the wells 426, until they are ready to be used. In such embodiments, the distal end of the DiTi 302 penetrates the respective sealing member as it is inserted into the proximal opening 112 of the cleaning member coupling element 104. In an alternative embodiment, the cleaning member wells 426 may be individually sealed, so that when a seal is broken to access and detachably couple with a respective cleaning member 100, cleaning members 100 seated in neighboring wells 426 remain substantially environmentally sealed. FIGS. 11A and 11B are side views, and FIG. 12 is a bottom view, respectively, of the cleaning member storage tray 424.

Figure 13:
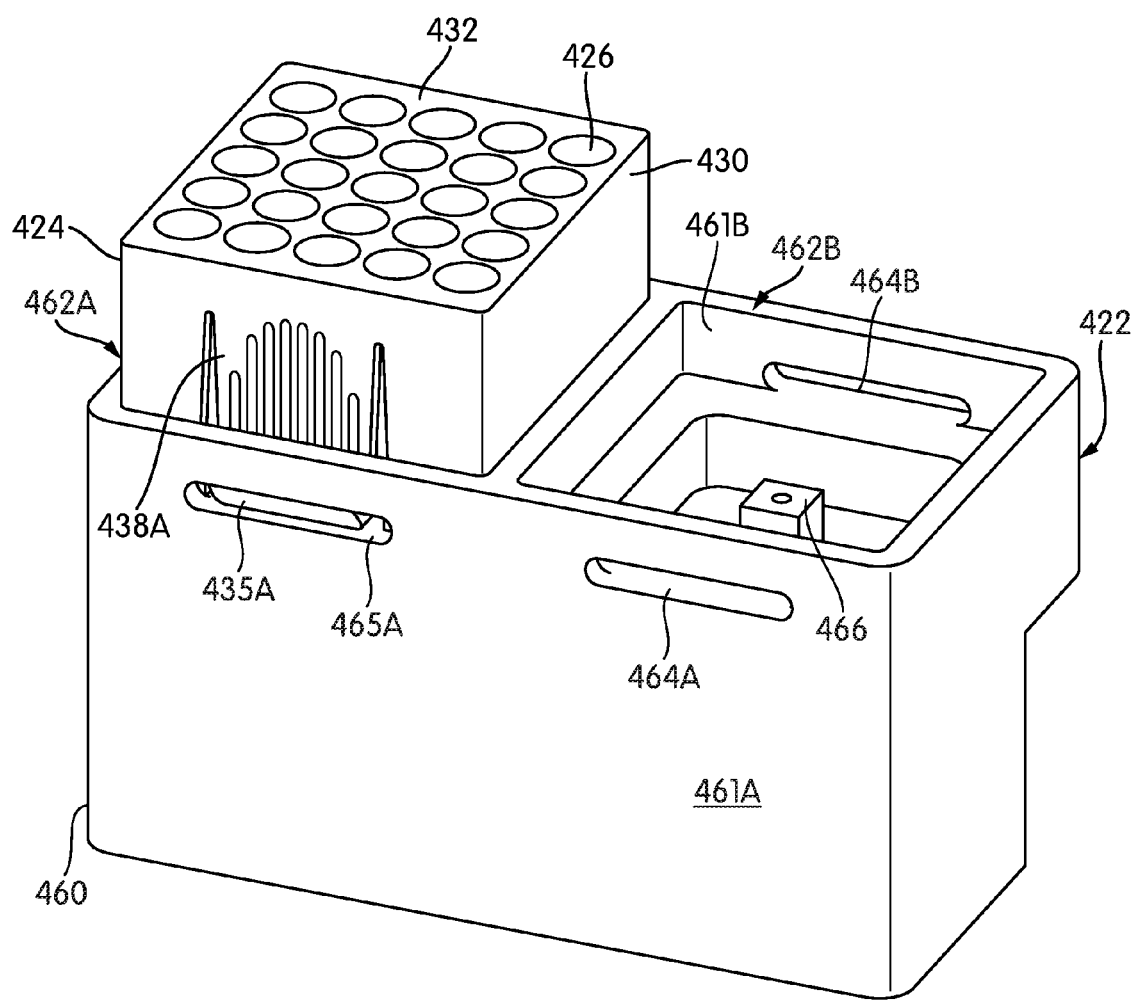
FIG. 13 is a perspective view of an exemplary cleaning member storage tray holder constructed according to embodiments disclosed herein.

FIG. 13 depicts an exemplary cleaning member storage tray holder 422 having a uni-body structure 460 molded out of a same or similar plastic material used to form the cleaning member coupling element 104 and/or storage tray 424, although other suitable materials and manufacturing techniques may be used for making the tray holder 422. The tray holder body 460 defines a side-by-side pair of recessed bays 462A and 462B, each bay 462A and 462B configured and dimensioned to receive a respective cleaning member storage tray 424 therein. A storage tray 424 is seated in bay 462A, with its horizontal latching flanges 435A and 435B extending through respective corresponding horizontal mating slots 465A and 465B disposed in opposing exterior walls 461A and 461B of the tray holder body 460. The latching flange 435B and horizontal mating slot 465B are not visible in FIG. 13. However, bay 462B is also provided with opposing horizontal mating slots 464A and 464B (both visible in FIG. 13) in the opposing walls 461A and 462B for latching a cleaning member tray 424 in the same manner.

It should be appreciated that the cleaning member storage tray 424 can be snap fit into the bay 462A due to the flexibility and resilience of tabs 438A and 438B of the storage tray body 425. In particular, tabs 438A and 438B of the storage tray 424 may be depressed or squeezed towards each other such that the tabs are displaced into the tray body 425 to allow the storage tray 424 to be fully inserted into the bay 462A. When the storage tray 424 is completely inserted into the bay 462A, the latching tabs 435A and 435B are aligned with the slots 465A and 465B, and the tabs 438A and 438B self-restore to a non-depressed configuration, causing the latching flanges 435A and 435B to at least partially extend into the respective mating slots 465A and 465B to thereby latch the storage tray 424 in bay 462A.

A teach member 466 is provided in a center area of bay 462B, and is used by the automated transport arm (not shown) to locate items it needs to interface with in the sample processing instrument deck (e.g., instrument deck 400' of FIG. 14) on which the sample receptacle tray holder 422 is mounted. The teach feature 466 in this embodiment has a box-like shape, although other shapes may be used. The automated transport arm will locate the feature by repeatedly driving down its distal tip until it force senses from the top to falling off the side. Once the transport arm locates all four sides of the teach feature 466, it interpolates the center position of the teach feature and knows the coordinates in X, Y, Z.

Referring to FIG. 14, the cleaning member tray holder 422, including a cleaning member storage tray 424 having twenty-five cleaning member wells 426, is shown installed by bracket 469 in an exemplary sample processing instrument deck 400' of a sample testing system. Except for the added cleaning member tray holder 422 (and cleaning member storage tray 424 mounted thereon) instrument deck 400' is essentially identical to instrument deck 400 of FIG. 6, including the provisioning and arrangement of a dozen test receptacle holders 408, each test receptacle holder 408 having five test receptacle wells 415 for seating sample test receptacles containing biological samples to be optically interrogated. One or more an automated transport arms (such as the above-described automated transport arm 300 of the embodiment of FIGS. 1-5, or the above-described transport arms 410 and 418 of FIG. 7) are associated with the instrument deck 400' (omitted from FIG. 14 for clarity).

It should be appreciated that the cleaning member storage tray(s) 424 may be manually placed into (and removed from) the storage tray holder 422. In alternative embodiments, the cleaning member storage tray(s) 424 may be robotically placed into (and removed from) the storage tray holder 422 by the respective automated transport arm employed for transporting the cleaning members 100. In the latter case, a modification may be made to/in the top surface of the tray to provide a coupling element for the automated transport arm, such as by converting the center-most cleaning member receptacle 426 into a recess configured for detachably coupling with the automated arm. The instrument deck 400' preferably also includes a waste output or other designated "used" cleaning member holder (not shown), configured to at least temporarily hold used cleaning members 100. Alternatively, the used cleaning members 100 can be returned to the same or a different cleaning member receptacle well 426 from which they were originally taken.

In accordance with the disclosed embodiments, a controller (not shown) controls operation of an automated transport arm associated with the instrument deck 400' (not shown in FIG. 14) for causing the automated transport arm to detachably couple with a respective cleaning member 100 (not shown in FIG. 14) held in a cleaning member receptacle 426 of the storage try 424, and to move the respective detachably-coupled cleaning member 100 into a position proximate to and/or contacting an optical element (e.g., the distal end of an optical fiber such as shown in FIGS. 4 and 5) underlying an open bottom end of one of the test receptacle wells 415 based upon one or both of a (i) predetermined cleaning schedule, and (ii) sensed presence of particulates and/or other materials disposed on or over the optical element. The controller may further cause the automated transport arm to deposit respective decoupled cleaning member 100 into a system waste output or a designated used cleaning member holder.

Although particular embodiments have been shown and described herein, it will be understood by those skilled in the art that they are not intended to limit the disclosure, and it will be obvious to those skilled in the art that various changes and modifications may be made (e.g., the dimensions of various parts) without departing from the scope of the disclosure, which is to be defined only by the following claims and their equivalents. The specification and drawings are, accordingly, to be regarded in an illustrative rather than restrictive sense.

The invention claimed is:

1. A sample testing system, comprising:
a test receptacle support structure;
an optical element positioned for transmitting electromagnetic radiation emitted or reflected by a sample disposed in a test receptacle supported by the test receptacle support structure;
a cleaning member; and
an automated transport arm configured to
detachably couple the cleaning member,
move the detachably-coupled cleaning member into a position proximate to and/or contacting the optical element, and
decouple the cleaning member.

2. The sample testing system of claim 1, wherein the automated transport arm is configured to deposit the decoupled cleaning member into a waste output.

3. The sample testing system of claim 1, wherein the automated transport arm comprises an articulating arm.

4. The sample testing system of claim 1, wherein the cleaning member comprises a proximal coupling element joined to a distal cleaning element, the coupling element having a proximal end portion configured to releasably mate with a distal working end portion of the automated transport arm.

5. The sample testing system of claim 4, wherein the coupling element and the cleaning element are separately molded components.

6. The sample testing system of claim 5, wherein a distal portion of the coupling element forms an interference fit with a proximal portion of the cleaning element.

7. The sample testing system of claim 5, wherein a distal portion of the coupling element forms a frictional fit with a proximal portion of the cleaning element.

8. The sample testing system of claim 4, wherein the coupling element and the cleaning element are co-molded as a single component.

9. The sample testing system of claim 4, wherein the automated transport arm is configured to move the detachably-coupled cleaning member into a position such that the cleaning element is inserted into a test receptacle well of the test receptacle support structure, and wherein the cleaning element is dimensioned such that an outer surface of the cleaning element conforms to an interior surface of the test receptacle well.

10. The sample testing system of claim 9, wherein the outer surface of the cleaning element and the interior surface of the test receptacle well have complementary frustoconical shapes.

11. The sample testing system of claim 9, wherein the cleaning element cleans, decontaminates and/or sterilizes the interior surface of the test receptacle well when inserted therein.

12. The sample testing system of claim 4, wherein:
the test receptacle well has an open bottom;
the optical element comprises an optical fiber having an end positioned proximate to the open bottom of the test receptacle well; and
the cleaning element cleans, decontaminates and/or sterilizes the end of the optical fiber when inserted into the test receptacle well.

13. The sample testing system of claim 4, wherein the cleaning element comprises an adhesive material.

14. The sample testing system of claim 13, wherein the adhesive material is selected from the group consisting of silicone, platinum cured silicone, thermoplastic polyurethane, thermoplastic elastomer, thermoplastic rubber, and a gel.

15. The sample testing system of claim 4, wherein the cleaning element comprises a material that generates a static attraction to particulates and/or other materials that can interfere with the transmission by the optical element of electromagnetic radiation emitted or reflected by the sample.

16. The sample testing system of claim 15, wherein the material that generates a static attraction is selected from the group consisting of silicon, polyvinyl chloride, polypropylene, polyethylene, polyurethane, polyester and polystyrene.

17. The sample testing system of claim 4, wherein the cleaning element comprises an absorbent material capable of retaining a fluid substance.

18. The sample testing system of claim 17, wherein the cleaning element retains the fluid substance, and wherein the fluid substance is selected from the group comprising isopropyl alcohol, ethyl alcohol, diluted hydrochloric acid, oxalic acid, diluted sodium hydroxide and diluted sodium hypochlorite.

19. The sample testing system of claim 1, further comprising a controller that controls operation of the automated transport arm for causing the automated transport arm to detachably couple with the cleaning member, and to move the detachably-coupled cleaning member into a position proximate to and/or contacting the optical element based upon one or both of a (i) predetermined cleaning schedule, and (ii) sensed presence of particulates and/or other materials disposed on or over the optical element.

20. The sample testing system of claim 1, further comprising one or more cleaning member holders, the cleaning member being one of a plurality of cleaning members, each of the cleaning members being held in a respective one of the one or more cleaning member holders.

21. The sample testing system of claim 20, wherein the automated transport arm is configured to selectively deposit the decoupled cleaning member into the same or a different cleaning member holder from which the decoupled cleaning member was removed.

22. A sample testing system, comprising:
one or more test receptacle holders, each test receptacle holder comprising a plurality of test receptacle wells, each test receptacle well having an open bottom end and configured to have a test receptacle seated therein;
a plurality of optical fibers arranged with respect to the one or more test receptacle holders, such that an end of a respective optical fiber is positioned proximate to the open bottom end of each test receptacle well to allow for transmission of electromagnetic radiation emitted or reflected by a sample contained in a test receptacle seated in the test receptacle well;
a cleaning member holder comprising a plurality of cleaning member wells, each of a plurality of the cleaning member wells configured for having a cleaning member seated therein; and
an automated transport arm configured to
detachably couple a cleaning member located in one of the cleaning member wells,
remove the detachably-coupled cleaning member from the respective cleaning member well,
insert a distal portion of the detachably-coupled cleaning member into one of the test receptacle wells, such that a distal end of the cleaning member is positioned proximate to or contacting the end of the optical fiber positioned proximate to the open bottom end of the respective test receptacle well,
remove the detachably-coupled cleaning member from the respective test receptacle, and
decouple the cleaning member.

23. A cleaning member for use in a sample testing system, comprising:
a proximal coupling element; and
a distal cleaning element, the coupling element having a proximal end portion configured to releasably mate with an automated transport arm.

24. A method of operating a sample testing system, the system comprising a test receptacle support structure and an optical element positioned for transmitting electromagnetic radiation emitted or reflected by a sample disposed in a test receptacle supported by the test receptacle support structure, the method comprising using an automated transport arm to:
detachably couple a cleaning member to a working end of the transport arm;
move the detachably-coupled cleaning member into a position proximate to and/or contacting the optical element, such that the cleaning member thereby cleans and/or sterilizes the optical element; and
decouple the cleaning member from the working end of the transport arm.

* * * * *